United States Patent [19]

Weitz et al.

[11] 4,239,910

[45] Dec. 16, 1980

[54] MANUFACTURE OF BUTENEDIOL DIESTERS

[75] Inventors: Hans-Martin Weitz, Bad Duerkheim; Rolf Platz, Mannheim; Juergen Hartig, Ludwigshafen, all of Fed. Rep. of Germany

[73] Assignee: BASF Aktiengesellschaft, Fed. Rep. of Germany

[21] Appl. No.: 779,284

[22] Filed: Mar. 18, 1977

[30] Foreign Application Priority Data

Mar. 18, 1976 [DE] Fed. Rep. of Germany ....... 2611423

[51] Int. Cl.³ ................... C07C 67/055; C07C 69/08; C07C 69/16
[52] U.S. Cl. ............................... 560/244; 260/346.11; 560/234; 568/858; 568/861
[58] Field of Search ..................... 260/410.6; 560/234, 560/1, 244, 245, 246, 243, 112

[56] References Cited

U.S. PATENT DOCUMENTS

| | | | |
|---|---|---|---|
| 3,755,423 | 8/1973 | Onoda et al. | 560/244 |
| 3,872,163 | 3/1975 | Shimizu et al. | 560/243 |
| 3,965,152 | 6/1976 | Smith et al. | 560/243 |
| 3,965,156 | 6/1976 | Smith et al. | 560/243 |

*Primary Examiner*—Vivian Garner
*Attorney, Agent, or Firm*—Keil & Witherspoon

[57] ABSTRACT

In a process for the manufacture of butenediol-dicarboxylic acid esters by reacting butadiene with oxygen and a carboxylic acid in the presence of a noble metal catalyst containing platinum or palladium, the carboxylic acid is added to the reaction mixture in the form of the ester of the acid with a low molecular weight aliphatic alcohol such as methanol and the reaction is carried out under conditions under which the ester undergoes hydrolysis, or the hydrolysis is carried out before the main reaction. This enables the carboxylic acid obtained on further processing of the butenediol esters to be recycled.

7 Claims, 1 Drawing Figure

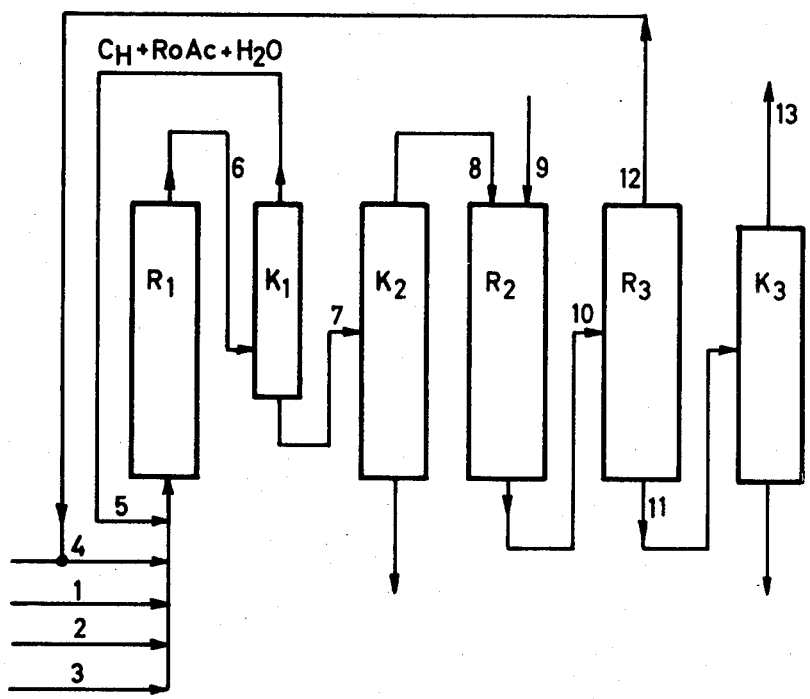

MANUFACTURE OF BUTENEDIOL DIESTERS

The present invention relates to a process for the manufacture of butenediol diesters, in particular but-1-ene-3,4-diol diformate or diacetate and/or but-2-ene-1,4-diol diformate or diacetate, by reacting butadiene and molecular oxygen with a carboxylic acid, in particular formic acid or acetic acid, in the presence of a noble metal catalyst. This reaction is commonly referred to as an acyloxylation or acetoxylation, the latter term being employed when acetic acid is used.

The invention further relates to a process for the manufacture of butanediol and/or tetrahydrofuran (THF) from but-2-ene-1,4-diol diesters.

The process to which the invention relates is disclosed, inter alia, in U.S. Pat. No. 3,755,423 and in German Laid-Open Application DOS 2,417,658, the former being incorporated herein by reference. The improvements in the process which have hitherto been described essentially concerned suitable catalysts and advantageous technological embodiments.

Butenediol diesters are intermediates for, inter alia, the manufacture of butane-1,4-diol for which a hydrolysis, with recovery of the carboxylic acid, must obviously be carried out (before or after hydrogenation of the olefinic double bond). The acid is usually recycled, various working-up sequences being interpolated.

A problem in such recycling is that, for reasons of shifting the equilibrium, the hydrolysis of the butenediol diester or butanediol diester must be carried out with a large excess of water and ultimately a reaction mixture which is difficult to separate and which contains butanediol with or without THF, water and, for example, acetic acid, is obtained. The non-ideal boiling characteristics of water/acetic acid mixtures are known to be the cause of the high energy consumption of this separation process. It is an object of the present invention to avoid this disadvantage.

We have found that this object is achieved and that the reaction of butadiene, molecular oxygen and, instead of the free acid, an ester of a carboxylic acid with a short-chain alcohol of, say, 1 to 4 carbon atoms, preferably methyl acetate, in the presence of a nobel metal catalyst leads to butenediol diesters if the reaction is carried out under conditions under which hydrolysis occurs, i.e., in the presence of a hydrolysis catalyst and of at least 1 mole of water per mole of butadiene to be converted, or if the ester is hydrolyzed prior to the reaction. Carboxylic acids, for the purpose of the present invention, are to be understood essentially as formic acid and, in particular, acetic acid; other carboxylic acids are of less interest, principally for economic reasons.

The hydrolysis may take place completely or partially prior to the reaction; in that case a mixture, for example the mixture, corresponding to the acid hydrolysis equilibrium, of the ester, the carboxylic acid, the alcohol and water, is fed to the actual reaction or acetoxylation.

Since the acid hydrolysis is an equilibrium reaction, it is advisable to carry out the actual acetoxylation reaction in the presence of the acid catalyst, the ester and water. In that case, the carboxylic acid is consumed and the equilibrium is shifted accordingly.

If a basic hydrolysis catalyst is used, separate hydrolysis, for example by means of a basic ion exchanger, may be more advantageous.

The latter point is mentioned because, surprisingly, the acetoxylation reaction will also take place in an alkaline medium, a fact which was previously not known.

In contrast to the information disclosed in U.S. Pat. No. 3,755,423, the reaction is insensitive to the presence of even substantial amounts of water; however, it is undesirable to have unnecessarily large amounts of water present, since these detract from the economics of the process. The reaction is therefore preferably carried out in the presence of an amount of water corresponding to that defined by the equation $H_2C=CH-CH=CH_2 + 2ROAc + 0.5O_2 + H_2O \rightarrow AcOCH_2-CH=CH-CH_2OAc + 2ROH$ (R being alkyl of 1 to, say, 4 carbon atoms and Ac being $CH_3CO-$), i.e., 1 mole of water per mole of butadiene, or not exceeding the latter by, e.g., more than 10 moles. Fundamentally, however, the feasibility of the process does not depend on the amount of water; as is known, major amounts of water shift the equilibrium amounts of alcohol, acid and ester in favor of the acid.

In view of the fact that the most important product desired from the reaction of butadiene with a carboxylic acid and oxygen is butane-1,4-diol or tetrahydrofuran, the invention further relates to the manufacture of butane-1,4-diol and/or THF by reacting butadiene with molecular oxygen and a carboxylic acid ester in the presence of an acid catalyst and of a noble metal catalyst, hydrogenating the resulting but-2-ene-1,4-diol diester to give the butanediol diester and hydrolyzing the latter, or subjecting it to a cyclizing reaction, the acid recovered being recycled. In this case, the invention consists in the fact that the hydrolysis of the butane,1,4-diol diester is carried out in the presealiphatic alcohol, in the form of a trans-esterification, and the alkyl ester obtained by trans-esterification is recycled (with or without purification) to the process. The aliphatic alcohol can remain in the reaction mixture over the entire reaction zone and does not interfere. Of course, the sequence of hydrogenation and hydrolysis can be interchanged, i.e., it is possible first to hydrolyze the butenediol diacetate and then to hydrogenate the butenediol obtained. It is advantageous to carry out the trans-esterification in the presence of a stationary excess of, for example, from 1 to 10 moles of the alcohol.

It is true that German Laid-Open Application 2,503,748 has disclosed that the reaction of ethylene, oxygen and acetic acid in the presence of a catalyst can also be carried out using methyl acetate and water if an acid co-catalyst is present. However, the said process is not comparable with the process of the invention, inter alia because the former uses a different, and substantially more active catalyst which requires some moderation; in this process, the addition of substantial amounts of water and the use of a preliminary hydrolysis process thus result in a lowering of the rate of reaction. Inherently, this conventional reaction does not, however, consume any water.

As far as the oxidative addition reaction of the carboxylic acid and butadiene (i.e. the acetoxylation) is concerned, the process of the invention is carried out in the presence of noble metal catalysts. For the purpose of the invention, noble metal catalysts are catalysts from the group of the platinum metals, especially palladium and platinum, which in addition contain a further metal selected from the group consisting of elements of group 5A and 6A of the periodic system of elements, such as selenium, tellurium, antimony or bismuth. The manufacture and use of the catalysts are described in detail in the publications mentioned at the outset which are herein incorporated by reference.

The acid catalyst required for hydrolyzing the alkyl ester may be of various kinds. For example, a certain amount of a previous ester hydrolysis mixture, or of the acid itself, may be used, these materials being soluble in the reaction mixture. A mineral acid may also be used as the catalyst.

It is also possible and advantageous to use solid acid catalysts, e.g., acid aluminum oxides, silicic acids, solid phosphoric acids (phosphoric acids absorbed on carriers) and certain ion exchangers possessing acidic groups; amongst these, crosslinked polystyrenesulfonic acids have been employed very successfully.

It is particularly advantageous to use macro-reticular styrenedivinylbenzene copolymers containing an amount of sulfonic acid groups (i.e. having a $H^+$ ion capacity) of up to 1.75 milliequivalent/ml. These copolymers have, for example, a particle size of from 0.4 to 0.5 mm and a tap density of 800 g/l, and possess good resistance to oxidation. These catalysts are obtained by polymerizing the monomers in certain solvents in which the polymers are insoluble and then sulfonating the polymer.

Acid aluminum oxides may also be used; the pH of a 10% strength aqueous suspension of these aluminum oxides is, for example 4; a suitable particle size is from 0.05 to 0.15 mm.

Suitable basic catalysts are basic ion exchangers, quaternary ammonium hydroxides and alkali metal hydroxides, alkali metal carbonates, and salts of alkalis with carboxylic acids which exhibit a basic reaction due to hydrolysis; the basic catalyst may also be introduced in the form of, for example, alkali metal alcoholates. Sodium and potassium are suitable alkali metals for the above purposes.

Depending on the process technology used, solid (hydrolysis) catalysts are suspended together with the (solid) noble metal catalysts in the reaction mixture, or arranged as a mixed bed, or accommodated in their own apparatus separate from the actual reaction chamber. In view of the presence of molecular oxygen during the acetoxylation reaction, it is at times advantageous to locate solid organic ion exchangers in a separate reaction chamber; in most cases, however, it is preferred to accommodate the catalyst in the actual reaction chamber.

The amount or concentration of the catalyst should be such that the rate of hydrolysis of the ester is greater, or at least not less, than the rate of the acetoxylation reaction. In the case of methyl acetate, this corresponds, for example, to a concentration of from 80 to 300 milliequivalents of acid per mole of ester converted per hour, i.e., at the conventionally achievable speeds of the main reaction, a degree of acidity of from 0.1-normal to 3-normal, or a corresponding amount of solid acid catalyst, suffices.

The reaction temperature corresponds to the conventional values for acetoxylation and is, for example, from 60° to 120° C. Because of the volatility of butadiene and oxygen, the reaction is in general carried out under a pressure of from atmospheric pressure to 200 bars. Instead of oxygen, gas mixtures containing oxygen, e.g., air, may be used. The reaction can be carried out in the absence of a gas phase, for example exclusively with dissolved oxygen and butadiene. Rates of conversion of 600 g of diester per 1,000 g of catalyst per hour are achieved.

Butenediol diacetate as a rule consists of an isomer mixture; when using suitable catalysts it contains, for example, 10% of but-1-ene-3,4-diol diacetate (vinylglycol diacetate) and 90% of a cis-trans isomer mixture of but-2-ene-1,4-diol diacetate. The mixture of the 1,4-diacetates is in general hydrogenated and the product is then hydrolyzed to give butanediol or THF.

The fact that the hydrogenated reaction mixture as a rule contains sufficient alcohol for a trans-esterficiation can be used, in a further embodiment of the invention, in order to recover the alkyl ester. Advantageously, the method followed is to heat the hydrogenated reaction mixture, together with the alcohol, in aqueous solution in the presence of a trans-esterification catalyst and to distil off the relatively low-boiling alkyl ester. Depending on the process conditions, the product obtained is an aqueous solution of butane-1,4-diol and/or tetrahydrofuran, from which the pure products are isolated in the usual manner. The lower alkyl acetates form an azeotrope with water, containing from about 5 to 10% of water. This is an advantage as far as the desired procedure is concerned; as mentioned at the outset, water is consumed in carrying out the acetoxylation. Accordingly, methyl acetate and ethyl acetate are preferred reactants. In principle, the process can also be carried out with the formic acid esters; for example, methyl formate is suitable.

The FIGURE shows an apparatus which can be used with advantage for carrying out the reaction.

According to this FIGURE, oxygen (1), water (2) and butadiene (3) together with an alkyl acetate (4), or those portions (5) thereof which have not been converted in the first pass, are fed to a reaction chamber ($R_1$) which may contain an acid ion exchanger and a palladium catalyst as a mixed bed; in a downstream column ($K_1$), the reaction mixture (6) is separated into unconverted materials (5) and the mixture of the diesters with certain amounts of monoesters and butanediol (7). These products are, if necessary, subjected to a preliminary purification ($K_2$) and are then hydrogenated ($R_2$) with hydrogen (9). The hydrogenated product mixture (10) is separated, in a reactor ($R_3$) operating as a distillation column, into butanediols (11) and a mixture of low-boiling products (12), containing alkyl ester and water, with or without alcohol, a trans-esterification taking place during this stage. The devices used to control this trans-esterification (alcohol recycling, acid dosing, reflux condenser and the like) have not been shown in the FIGURE. The desired product, i.e., butanediol (13), is subjected to a fine purification ($K_3$).

EXAMPLE 1

400 g (5.4 g mole) of methyl acetate, 50 ml of liquid butadiene, 96 g (5.3 g mole) of water, 10.3 g of a commercial ion exchanger, based on a crosslinked polystyrenesulfonic acid, in the $H^+$ form and 6 g of a catalyst which contained 5.9%, based on the total weight of the catalyst, palladium and 1.0% of tellurium on commercial active charcoal (particles of from 0.8 to 1 mm diameter) were sealed in a 1 liter stirred autoclave and heated at 85° C. under reflux after having set up a pressure of 20 bars by introducing an appropriate amount of oxygen.

The duration of the experiment was 4 hours. The autoclave was then let down and the liquid contents were filtered and distilled.

The numerical data shown in Table 1 below relate, inter alia, to this Example 1, the yield and rate of reaction being expressed in terms of the sum of all the isomers formed, including any butenediol monoester and butenediol which may be formed (for a typical composition of the reaction product, compare Table 2).

EXAMPLES 2 to 9

The procedure followed was as described in Example 1. Where changes in conditions compared to Example 1 have to be recorded, they are shown in Table 1. The experiments under atmospheric pressure were carried out by passing 3 l (S.T.P.) of oxygen and 3 l (S.T.P.) of butadiene per hour under atmospheric pressure into the autoclave and releasing residual gas, as necessary, through a reflux condenser.

1,440 mm long and having an internal diameter of 35 mm), and 21 g of methanol and 0.9 g of sodium methylate are added per hour.

Using a bottom temperature of 136° C. and a reflux ratio of 3.0, 97 g of butane-1,4-diol and butane-1,2-diol, in the weight ratio of 9:1, are obtained per hour. Over the same period of time, 60 g of a mixture of 76.5% of methyl acetate and 23.5% of methanol are formed as the distillate and are recycled to the reaction mixture at the inlet to the apparatus.

If the bottom temperature of the said column is changed to from 165° to 170° C., tetrahydrofuran (THF) is formed, so that the bottom residue only contains butane-1,2-diol. The THF can be isolated from the distillate in the usual manner.

EXAMPLES 11 to 15

To carry out the reaction in an alkaline medium, or in the presence of a basic hydrolysis catalyst, the procedure described in Example 1 was followed using first an acid ion exchanger and then various basic catalysts. The palladium catalyst was present on charcoal as a carrier (6 g in each case) and contained 7.5% of Pd and 1.4% of tellurium. The particular size was from 0.1 to 0.3 mm. In each case, 400 g of methyl acetate, 96 g of water and 50 ml of liquid butadiene were reacted under an oxygen pressure of 20 bars, at 85° C.

Table 3 shows the result.

Table 4 shows the composition of the reaction product formed in Example 15.

TABLE 1

| Example | Ester+ [g] | Water [g] | Catalyst or composition [g] | T [°C.] | Duration of experiment [h] | Pressure [bars] | Rate of reaction [g/kg . h] |
|---|---|---|---|---|---|---|---|
| 1 | 400 MeAc | 96 | 6 g | 85 | 4 | 20 | 540 |
| 2 | 400 MeAc | 96 | 6 g (5.2% of platinum, 0.9% of tellurium and 0.073% of nickel on active charcoal) | 85 | 4 | 20 | 435 |
| 3 | 400 MeAc | 96 | 12.5 g (catalyst* used 100 hours) | 85 | 4 | 20 | 500 |
| 4 | 490 MeAc | 10 | as for 1 | 56 | 4 | 0 | 34 |
| 5 | 446 MeAc | 96 | as for 3 | 58 | 4 | 20 | 540 |
| 6 | 400 MeAc | 11.3 | as for 1 | 85 | 4 | 20 | 49 |
| 7 | 400 MeAc | 8.3 | as for 1 | 85 | 4 | 20 | 25 |
| 8 | 400 EAc | 96 | as for 1 | 85 | 4 | 20 | 264 |
| 9 | 324 MeF | 96 | as for 1 | 85 | 4 | 20 | 71 |

+MeAc = methyl acetate
*according to Example 1
EAc = ethyl acetate
MeF = methyl formate

TABLE 2

1.9% of but-1-ene-3,4-diol diacetate
11.7% of but-1-ene-3,4-diol monoacetate
—% of but-1-ene-3,4-diol
4.3% of cis-but-2-ene-1,4-diol diacetate
40.8% of trans-but-2-ene-1,4-diol diacetate
2.2% of cis-but-2-ene-1,4-diol monoacetate
26.7% of trans-but-2-ene-1,4-diol monoacetate
1.4% of but-2-ene-1,4-diol (sum of cis+trans)

EXAMPLE 10

200 ml of the palladium catalyst described in Example 1 and 200 ml of an acid ion exchanger (obtainable under the tradename Amberlite 200) which is based on a macro-reticular polystyrenesulfonic acid, are filled into a reactor. The latter consists of a pressure-resistant double-jacket tube having a length of 2 m and an internal diameter of 20 mm and forms part of an apparatus as shown in the accompanying drawing where it is marked $R_1$.

Per hour, 4 l of methyl acetate, 1 l of water, 500 ml of liquid butadiene and 20 l (S.T.P.) of oxygen are passed from below into the reactor, under 30 bars pressure, at from 85° to 90° C. The reaction mixture which issues is let down, the butadiene is separated off and the residue is hydrogenated in the usual manner.

The hydrogenated mixture is fed to the 9th tray of an experimental column having 20 trays (column being

TABLE 3

| Example | Base/acid | Duration of experiment [h] | Rate of reaction |
|---|---|---|---|
| 11 | 10 g of acid ion exchanger (H+ form) | 0.5 | 64.5 |
| 12 | as for 11 | 1.0 | 78 |
| 13 | 20 g of NaOAc | 4.0 | 158 |
| 14 | 20 g of NaOCH$_3$ | 4.0 | 59 |
| 15 | 10 g of basic ion exchanger (OH form) | 4.0 | 328 |

TABLE 4

1.1% of but-1-ene-3,4-diol diacetate
7.2% of but-1-ene-3,4-diol monoacetate
29.1% of but-1-ene-3,4-diol
11.4% of but-2-ene-1,4-diol diacetate
18.7% of but-2-ene-1,4-diol monoacetate 29.4% of but-2-ene-1,4-diol.

We claim:

1. In a one-step liquid phase process for the manufacture of butenediol diesters by reacting liquid butadiene, molecular oxygen and a carboxylic acid in a reaction chamber and in the presence of an effective amount of an acyloxylation catalyst containing platium or palladium, the improvement which comprises:

using an ester of the carboxylic acid with a short-chain aliphatic alcohol in place of the carboxylic acid and carrying out the reaction in the presence of an effective amount of a hydrolysis catalyst and at least 1 mole of water per mole of butadiene to be converted.

2. A process as set forth in claim 1, wherein methyl acetate or ethyl acetate is used as the ester.

3. A process as set forth in claim 1, wherein an acid ion exchanger is used as the hydrolysis catalyst.

4. A process as set forth in claim 1, wherein the acyloxylation catalyst in addition contains tellurium and is present on an active charcoal carrier.

5. A process as set forth in claim 1, wherein the ester of the carboxylic acid with the short-chain aliphatic alcohol is obtained by hydrogenating the butenediol diester to give butanediol diester and hydrolyzing the butanediol diester in the presence of a short-chain aliphatic alcohol.

6. A process as set forth in claim 1, wherein the hydrolysis catalyst is a macro-reticular styrene-divinylbenzene copolymer containing an amount of sulfonic acid groups of up to 1.75 meq/ml.

7. A process as set forth in claim 1, wherein the hydrolysis catalyst is a crosslinked polystyrene sulfonic acid.

* * * * *